(12) United States Patent
Hickey

(10) Patent No.: US 9,157,100 B2
(45) Date of Patent: Oct. 13, 2015

(54) INTEGRATED PROCESSES FOR BIOCONVERTING SYNGAS TO OXYGENATED ORGANIC COMPOUND WITH SULFUR SUPPLY

(75) Inventor: Robert Hickey, Okemos, MI (US)

(73) Assignee: Coskata, Inc., Warrenville, IL (US)

( * ) Notice: Subject to any disclaimer, the term of this patent is extended or adjusted under 35 U.S.C. 154(b) by 462 days.

(21) Appl. No.: 13/525,079

(22) Filed: Jun. 15, 2012

(65) Prior Publication Data
US 2013/0337513 A1 Dec. 19, 2013

(51) Int. Cl.
| | | |
|---|---|---|
| C12P 7/00 | (2006.01) | |
| C12P 5/00 | (2006.01) | |
| C12P 11/00 | (2006.01) | |
| C12P 7/06 | (2006.01) | |
| C12P 5/02 | (2006.01) | |

(52) U.S. Cl.
CPC ............... *C12P 7/065* (2013.01); *C12P 5/023* (2013.01); *C12P 7/00* (2013.01); *C12P 11/00* (2013.01); *Y02E 50/17* (2013.01)

(58) Field of Classification Search
None
See application file for complete search history.

(56) References Cited

U.S. PATENT DOCUMENTS

| 4,200,523 A | 4/1980 | Balmat |
|---|---|---|
| 5,173,429 A | 12/1992 | Gaddy et al. |
| 6,136,577 A | 10/2000 | Gaddy |
| 7,704,723 B2 | 4/2010 | Huhnke et al. |
| 8,143,037 B2 | 3/2012 | Zahn et al. |
| 2007/0275447 A1 | 11/2007 | Lewis et al. |
| 2008/0032375 A1 | 2/2008 | Hartmann et al. |
| 2008/0220489 A1 | 9/2008 | Offerman |
| 2008/0302272 A1 | 12/2008 | Allen et al. |
| 2009/0227003 A1 | 9/2009 | Blotsky et al. |
| 2010/0221804 A1 | 9/2010 | Veit et al. |

OTHER PUBLICATIONS

Das, A. and L.G. Ljungdahl, Electron Transport System in Acetogens and by Drake, H.L. and K. Kusel, Diverse Physiologic Potential of Acetogens, appearing respectively as Chapters 14 and 13 of Biochemistry and Physiology of Anaerobic Bacteria, L.G. Ljungdahl eds,. Springer (2003).
"Evidence for Production of n-Butanol from Carbon Monoxide by Butyribacterium methylotrophicum," Journal of Fermentation and Bioengineering, vol. 72, 1991, p. 58-60.
"Production of butanol and ethanol from synthesis gas via fermentation," Fuel, vol. 70, May 1991, p. 615-619.
*Clostridium autoethanogemum*sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351.
Electrodialysis (ED) and Electrodialysis Reversal (EDR), U.S. Department of the Interior, Bureau of Reclamation, Sep. 20, 2010.

*Primary Examiner* — Kade Ariani
*Assistant Examiner* — Charles Zoltan Constantine

(57) ABSTRACT

Integrated processes are provided for the bioconversion of syngas to oxygenated organic compound with the ability to recycle sulfur nutrient and generate sulfur nutrient to the syngas fermentation in a safe and cost-effective manner. In preferred aspects of the invention, an acidogenic digestion is used to provide a biogas containing hydrogen sulfide, and then a methanogenic fermentation can follow to provide a methane-containing biogas that has a low hydrogen sulfide concentration.

17 Claims, 2 Drawing Sheets

INTEGRATED PROCESSES FOR BIOCONVERTING SYNGAS TO OXYGENATED ORGANIC COMPOUND WITH SULFUR SUPPLY

FIELD OF THE INVENTION

This invention pertains to integrated processes for bioconverting syngas to oxygenated organic compound such as ethanol, propanol and butanol and generation of at least a portion of the sulfur nutrient for microorganisms for the bioconversion. More particularly, the integrated processes are attractive from capital and energy costs standpoints as well as avoiding costs to procure sulfur nutrient.

BACKGROUND

Microorganisms used in metabolic processes require nutrients and micronutrients. One of the required nutrients is a source of reduced sulfur, usually in the form of a sulfide such as cysteine. Hydrogen sulfide has been found in many instances to be a source of reduced sulfur for use by the microorganisms. Although hydrogen sulfide is less expensive than, say, cysteine, it is toxic and thus requires special handling and is particularly dangerous in pure form. Accordingly, if hydrogen sulfide is to be a viable source of reduced sulfur, generation at the site of the fermentation at the rate required to avoid significant storage of hydrogen sulfide would be desired.

Numerous processes exist that generate hydrogen sulfide, either as the sought product or as a contaminant in another process. For instance, Velt, et al., in U.S. Patent Publication No. 2010/0221804 propose an integrated ethanol and biogas system where thin stillage is processed to generate a biogas. At paragraph 0028, the applicants state that the biogas contains methane and carbon dioxide and can also include hydrogen, hydrogen sulfide and ammonia. They suggest that the biogas can be used for heating or operating various types of engines to produce mechanical or electrical power.

Although hydrogen sulfide can be recovered from gas streams, processes for the recovery necessarily incur capital and operating costs. These costs thus reduce the attractiveness of these hydrogen sulfide-containing gas streams being a source of sulfur for fermentation processes.

Offerman, in U.S. Published Patent Application No. 2008/0220489 discloses a process in which biogas is generated from wastes, such as manure, and the biogas is converted to syngas for synthesis of liquid fuels. The applicant discusses the use of $Fe^{+2}$ from iron-reducing microorganisms in the fermentation to generate the biogas or amine-containing resin to reduce the concentration of hydrogen sulfide in the biogas, and thus in the ultimate fuel product.

Balmat, in U.S. Pat. No. 4,200,523 discloses processes for removing sulfate ions from dilute aqueous streams by contact with Desulfovibrio sulfate-reducing bacteria to convert the sulfate to sulfide and removing the sulfide ions. The use of an electron donor (gaseous hydrogen) is required.

Processes are sought to enhance the economics of syngas fermentation to produce oxygenated organic compound where reduced sulfur nutrient can be effectively and inexpensively supplied by the processes at an as needed rate.

SUMMARY OF THE INVENTION

By this invention processes are provided for the bioconversion of syngas to oxygenated organic compound such as ethanol, propanol, and butanol where the supply of reduced sulfur nutrient is integrated into the process. The supply of reduced sulfur nutrient is derived from a metabolic process using feeds streams from the bioconversion of syngas to produce a hydrogen sulfide-containing gas that can be directly provided to the fermentation medium used for the bioconversion of syngas.

In one aspect, reduced sulfur nutrient is obtained as a hydrogen sulfide-containing gas from the metabolic degradation of biosolids obtained from the fermentation medium used for the bioconversion of syngas. Often, at least about 30, and sometimes up to 50 percent or more of the sulfur nutrient for the bioconversion of syngas can be recovered from the biosolids recovered from the fermentation medium. This recovery of sulfur nutrient represents a significant savings itself. However, the processes of this invention enable sulfur nutrient to be generated from readily available, less toxic and less expensive sources of sulfur, namely sulfoxy moieties. Where used in combination, substantially the entire reduced sulfur nutrient requirements for the bioconversion of syngas can be achieved. These aspects of the invention may be used singularly or preferably in combination. In the aspect of the invention where sulfoxy moieties are metabolized to hydrogen sulfide, adequate electron donor may inherently be provided by the biomass from which hydrogen sulfide is recovered, and in the absence of, or in addition to, the presence of biomass, at least one of syngas and off-gas provides electron donor.

Through the integration reduced sulfur is able to be provided to the fermentation medium for the conversion of syngas in an economically attractive manner. Especially attractive embodiments of this invention enhance the yield of oxygenated organic compound and can provide a methane-containing biogas with a low hydrogen sulfide concentration.

In accordance with one aspect of the processes of this invention, solid debris including microorganisms used for the bioconversion of syngas to oxygenated organic compound are subjected to anaerobic digestion which provides a biogas containing hydrogen sulfide as well as other components such as carbon dioxide and water vapor. The biogas is directly provided to the aqueous fermentation broth for the syngas bioconversion. As the volume of the biogas is relatively small in comparison to the volume of syngas being introduced into the fermentation broth, the operation of the fermentation to bioconvert syngas is not adversely affected. Moreover, as the hydrogen sulfide is dilute in the biogas, reduced risks in handling and introduction into the fermentation broth are obtained. The gases diluting the hydrogen sulfide can pass through the fermentation broth and be ultimately discharged as a tail gas.

A metabolic process, which may or may not be an anaerobic digestion, may be used to convert oxidized forms of sulfur (sulfoxy moieties) or elemental sulfur to hydrogen sulfide. Electron donor for the metabolic process to bioconvert sulfoxy moieties to hydrogen sulfide is derived from the bioconversion of syngas process such as off gas containing at least one of unreacted hydrogen and carbon monoxide or aqueous streams or biosolids derived from the fermentation medium for the bioconversion of syngas. Advantageously syngas or gas effluent from the syngas fermentation is passed to the metabolic process to convert sulfoxy moieties in that not only is electron donor provided but also the gas serves as a sweep gas and dilutes the hydrogen sulfide.

One broad aspect of the processes of this invention pertains to processes for bioconversion of syngas to oxygenated organic compound with integrated hydrogen sulfide supply and comprises:

a. passing syngas into a syngas reactor containing aqueous fermentation broth under fermentation conditions, said fermentation broth containing microorganisms adapted for bioconverting syngas to oxygenated organic compound, to produce oxygenated organic compound dissolved in the fermentation broth and an off gas;
b. removing from the syngas reactor at least an aliquot portion of the fermentation broth containing oxygenated organic compound and containing biosolids;
c. separating from said aliquot portion of the fermentation broth an aqueous biosolids-containing phase containing biosolids having a higher solids content and a reduced oxygenated organic compound concentration than said aliquot portion;
d. subjecting the biosolids-containing phase to anaerobic digestion conditions to biodegrade solids in the aqueous liquid phase to provide an aqueous degraded solids product and a biogas product comprising hydrogen sulfide; and
e. passing at least an aliquot portion, say, at least about 75 volume percent to preferably substantially all, of the biogas to the syngas reactor to provide at least a portion of sulfur nutrient for the microorganisms.

In one embodiment of the processes of this invention, sulfoxy moiety or elemental sulfur is supplied to step (d) in an amount sufficient to provide a biogas containing the sought amount of hydrogen sulfide to meet the nutrient needs of the microorganisms in the reactor. Sulfoxy moieties include, but are not limited to sulfur dioxide, sulfamide and oxyanions of sulfur such as sulfate, sulfite, sulfamate and thiosulfate. Where the sulfoxy moiety is provided by sulfuric acid or sulfurous acid, maintaining the sought pH is facilitated.

The anaerobic digestion conditions to provide a biogas comprising hydrogen sulfide may be methanogenic or acidogenic. Methanogenic digestion is typically operated at a pH of between about 6.8 and 7.6. Acidogenic digestion conditions are frequently preferred for the anaerobic digestion to produce the hydrogen sulfide-containing biogas. Acidogenic digestion conditions generally do not produce methane, but rather provide a degradation to organic acids such as acetic acid. The acidogenic digestion thus provides several advantages. First, the biogas will not be diluted with methane. Although methane is inert in the syngas fermentation and would be a very small component of the tail gas from the reactor, the acidogenic digestion allows biosolids to be treated in a subsequent methanogenic, anaerobic digester to provide a biogas having a higher energy density and lower sulfur content. Second, the organic acids generated in the acidogenic digestion may be recovered and passed to the syngas reactor for bioconversion to oxygenated organic compound. Third, usually acidogenic digestion conditions provide for a greater conversion of sulfur contained in the biomass or as provided by sulfoxy moieties to hydrogen sulfide as opposed to HS$^-$ by maintaining the pH more acidic than the pKa of hydrogen sulfide. Typically acidogenic conditions comprise a pH of about 6, say 4.5 or 5 to 6.

Preferably where an acidogenic conditions are used for the anaerobic digestion, the aqueous degraded solids product is subjected to a subsequent anaerobic, methanogenic digestion to provide a biogas containing methane. As hydrogen sulfide has been removed during the acidogenic fermentation, the biogas from the methanogenic digestion can be relative free of hydrogen sulfide and thus may be directly useful as a gas to generate heat by combustion or to power engines. In some instances, the concentration of hydrogen sulfide in the methane-containing biogas is less than about 100, preferably less than about 20, parts per million by volume (ppmv).

Another broad aspect of the processes of this invention pertains to processes for bioconversion of syngas to oxygenated organic compound with integrated hydrogen sulfide supply comprises:
a. providing sulfoxy moiety to a sulfoxy bioreactor containing an aqueous metabolizing broth containing microorganisms capable of reducing sulfoxy moiety to hydrogen sulfide in the presence of electron donor, said metabolizing broth being at metabolizing conditions and providing a hydrogen sulfide-containing biogas;
b. providing syngas to a syngas bioreactor containing an aqueous fermentation medium capable of bioconverting syngas to oxygenated organic compound, said fermentation medium being at fermentation conditions to provide a fermentation broth containing oxygenated organic compound and bio solids and to provide an off gas containing at least one of hydrogen and carbon monoxide;
c. providing to the sulfoxy bioreactor an electron donor from step b, preferably at least one of an aliquot portion of the syngas to be provided to the syngas bioreactor, at least an aliquot portion of the off gas from the syngas bioreactor, at least a portion of the biosolids contained in the syngas bioreactor, and at least a portion of the fermentation medium from the syngas bioreactor, in an amount sufficient to provide electron donor to provide the hydrogen sulfide containing gas; and
d. passing at least an aliquot portion of the hydrogen sulfide-containing biogas to the syngas bioreactor.

The portion of the biosolids that may be provided to the sulfoxy bioreactor may be obtained from the fermentation medium in any suitable manner and may contain live microorganisms or dead microorganisms and other solid debris. The biosolids may be directly separated from the fermentation broth or may be indirectly separated such as by being contained in a distillation bottoms from a distillation to recover oxygenated organic compound from fermentation broth.

DETAILED DISCUSSION

As used herein, the term oxygenated organic compound means one or more organic compounds containing two to six carbon atoms selected from the group of aliphatic carboxylic acids and salts, alkanols and alkoxide salts, and aldehydes. Often oxygenated organic compound is a mixture of organic compounds produced by the microorganisms contained in the aqueous menstruum. Preferred oxygenated organic compounds are ethanol, n-propanol, i-propanol, n-butanol, i-butanol and acetone.

Also, the term syngas is a gas containing carbon monoxide and frequently hydrogen, although term "syngas", for purposes herein, is also intended to encompass carbon monoxide gas streams that may have little or no hydrogen. Typically, carbon monoxide is present in an amount of at least about 20 volume percent, and the syngas typically contains other components in addition to hydrogen such as carbon dioxide, nitrogen and water vapor. Syngas may derived from various sources, including, but not limited to, gasification of carbonaceous feedstocks such as biomass, landfill gas, coal, natural gas, and petroleum; coke gas and gas from other industrial operations such as petroleum refining and steel mill waste gas.

Figure 1:
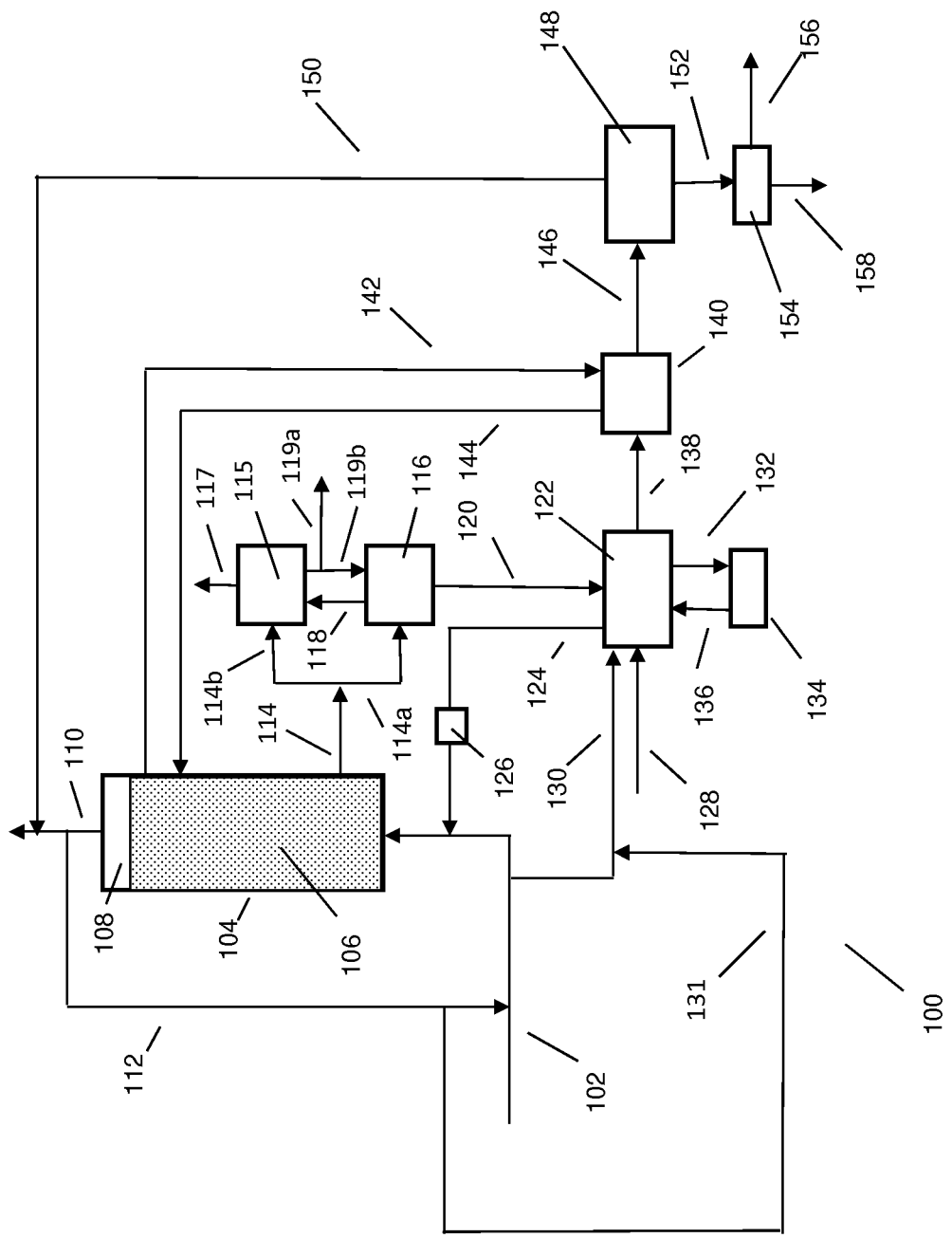
FIG. 1 is a schematic depiction of an apparatus capable of being used in accordance with the processes of this invention.

The integrated processes of this invention will be further described by reference to the FIG. 1. FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering. FIG. 1 also omits ancillary unit operations. The process and operation of FIG. 1 will be described in the context of the recovery and production of ethanol. The process is readily adaptable to making other oxygenated products such as acetic acid, butanol, propanol and acetone.

Syngas is provided to apparatus 100 via line 102. Syngas may derived from various sources, including, but not limited to, gasification of carbonaceous feedstocks such as biomass, landfill gas, coal, natural gas, and petroleum; coke gas and gas from other industrial operations such as petroleum refining and steel mill waste gas. The source of the syngas is not critical to the broad aspects of this invention. The syngas should, however, be free of components in concentrations that would be unduly adverse to the microorganisms used in the fermentation such as, but not limited to, hydrogen cyanide, alkenes, and alkynes and that would be adverse if present in the sought oxygenated organic compound such as tars and aromatics where ethanol is the sought product. Often the syngas contains 25 to 70, say, 40 to 65, mole percent carbon monoxide; 0 to 70, say, 30 or 40 to 65, mole percent hydrogen; and 1 to 20, say 3 to 15, mole percent carbon dioxide excluding nitrogen and water vapor from the concentration calculations.

The syngas in line 102 is passed to reactor 104 containing fermentation broth 106. Fermentation broth is maintained under fermentation conditions and the syngas is provided therein in a manner to enhance mass transfer of hydrogen and carbon monoxide to the aqueous broth for bioconversion by microorganisms to oxygenated organic compound. The fermentation may be on a continuous or batch basis. Preferably the syngas is continuously supplied.

One or more microorganisms may be used in the fermentation menstruum to produce the sought oxygenated organic compound. Bioconversions of CO and $H_2/CO_2$ to acetic acid, propanol, butanol, butyric acid, ethanol and other products are well known. For example, a description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds, Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704, 723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edmond-Jacques Nyns, Arch Microbiol., 1994, 345-351; Archives of Microbiology 1994, 161: 345-351; and *Clostridium Coskatii* having the identifying characteristics of ATCC No. PTA-10522 described in U.S. Pat. No. 8,143,037 B1. All of these references are incorporated herein in their entirety.

Suitable microorganisms for bioconversion of syngas to oxygenated organic compound generally live and grow under anaerobic conditions, meaning that dissolved oxygen is essentially absent from the fermentation liquid. Adjuvants to the aqueous menstruum may comprise buffering agents, trace metals, vitamins, salts etc. Adjustments in the menstruum may induce different conditions at different times such as growth and non-growth conditions which will affect the productivity of the microorganisms. U.S. Pat. No. 7,704,723, hereby incorporated by reference in its entirety, discloses the conditions and contents of suitable aqueous menstruum for bioconversion CO and $H_2/CO_2$ using anaerobic microorganisms.

Anaerobic fermentation conditions include a suitable temperature, say, between 25° and 60° C., frequently in the range of about 30° to 40° C. The conditions of fermentation, including the density of microorganisms, aqueous menstruum composition, and syngas residence time, are preferably sufficient to achieve the sought conversion efficiency of hydrogen and carbon monoxide and will vary depending upon the design of the fermentation reactor and its operation. The pressure may be subatmospheric, atmospheric or super atmospheric, and is usually in the range of from about 90 to 1000 KPa absolute and in some instances higher pressures may be desirable for biofilm fermentation reactors. As most reactor designs, especially for commercial scale operations, provide for a significant height of aqueous menstruum for the fermentation, the pressure will vary within the fermentation reactor based upon the static head.

The fermentation reactors used in this invention may be of any suitable design; however, preferably the design and operation provides for a high conversion of carbon monoxide and hydrogen to oxygenated organic compound. Fermentation reactors include, but are not limited to, bubble column reactors; jet loop reactors; stirred tank reactors; trickle bed reactors; biofilm reactors; moving bed reactors; membrane reactors and static mixer reactors including, but not limited to, pipe reactors.

As shown, reactor 104 has head space 108 containing off-gas which is unreacted hydrogen, carbon dioxide and carbon monoxide, and inerts such as methane and nitrogen. Off-gas is withdrawn via line 110. A portion of the off-gas, if desired, can be recycled via line 112 to increase the conversion of syngas to product.

Intermittently or continuously an aliquot portion of the fermentation broth 106 is withdrawn via line 114. Where the fermentation is a batch fermentation, essentially all the fermentation broth would be removed at one time. The portion withdrawn in a continuous operation is sufficient to maintain the oxygenated organic compound concentration in the fermentation broth below that which unduly adversely affects the microorganisms.

As shown, all or a portion of the withdrawn fermentation broth can be directly passed via line 114a to separator 116 which may be a decanter, filter, centrifuge or hydrocyclone to provide an aqueous liquid phase containing oxygenated organic compound and having a substantial absence of solids and a solids-containing phase which is usually a slurry, e.g., from between about 25 to 90, mass percent solids (excluding water contained in the solids). The aqueous liquid phase is passed via line 118 to product recovery operations 115 which can comprise one or more of distillation, membrane separators, and the like. For purposes of this description, product recovery operations 115 shall be referred to as distillation assembly 115. Alternatively, or in addition, all or a portion of the withdrawn fermentation broth can be directed via line 114b to distillation assembly 115.

Distillation assembly 115 comprises one or more distillation columns and a still bottoms separator. Ethanol is recovered via line 117. If a solids-containing portion of the fermentation broth is provided via line 114b to distillation assembly 115, then a solids-containing phase, which contains dead cells (due to the temperature conditions of the still) and solid proteins is withdrawn via line 119b and sent to separator 116. Otherwise the bottoms fraction is removed via line 119a.

The solids-containing phase is passed from separator 116 via line 120 to anaerobic digester 122. If desired, a portion of the solids-containing phase can be returned to reactor 104 by a suitable line (not shown). If so, the portion returned should enable an average cell retention to be maintained at a desired level to provide a balance between productivity and cell growth and rejuvenation rates.

Anaerobic digester 122 is maintained under anaerobic conditions for the sought catabolic activity. Any suitable microorganism for the digestion of biomass can be used. In one preferred embodiment of the invention, anaerobic digester 122 is maintained under acidogenic digestion conditions. Microorganisms for bioconversion of biomass to carboxylic acids such as formic, acetic, propionic, butyric and lactic acids under anaerobic conditions are well known. Often the anaerobic digester is self-inoculated. The conditions for the anaerobic digestion can vary depending upon the microorganisms used. Often, the temperature is between 25° and 60° C., frequently in the range of about 30° to 40° C. The pressure may be subatmospheric, atmospheric or super atmospheric, and is usually in the range of from about 90 to 1000 kPa absolute. Preferably the pH is maintained at or below about 6 such that free hydrogen sulfide is favored. digester 122 may be of any suitable design and is usually a stirred tank reactor.

Where anaerobic digester 122 is operated under methanogenic conditions, the residence time in the digester is usually sufficient to achieve the sought degradation of the solids to provide a solids mass that can be sent to disposal. Where anaerobic digester is an acidogenic digester and is to be followed by a methanogenic digester, the operator may elect to maintain the residence time sufficient to achieve a desired recovery of hydrogen sulfide or a desired production of carboxylic acid.

Anaerobic digester produces a biogas which is withdrawn via line 124. The biogas composition will depend upon the nature of the anaerobic digestion. For conventional anaerobic digestion, the biogas will frequently contain about 50 to 70 volume percent methane, about 25 to 45 volume percent carbon dioxide with the balance being primarily water vapor and hydrogen sulfide. Acidogenic digestion generally provides a biogas relatively free of methane which contains 40 to 90 volume percent carbon dioxide with the balance being hydrogen, water vapor and hydrogen sulfide.

Biogas in line 124 is passed through device 126 to remove any carry over microorganisms and is directed to reactor 104. Device 126 can be a filter or any other method that allows the gas stream to remove microorganisms, and preferably viruses, or otherwise be sterilized prior to going to the syngas fermentation system. The advantage of the invention is that the biogas is not treated to remove hydrogen sulfide. Moreover, with the hydrogen sulfide being dilute in the biogas, handling and safety risks are reduced. Even though the hydrogen sulfide is being provided in a dilute form, often containing between about 500 and 100,000 ppmv hydrogen sulfide, the low molar flow rate of the biogas, often less than about 2, and most often less than about 1, percent of the molar flow rate of the syngas feed, there is no appreciable adverse effect on the syngas fermentation.

Anaerobic digester 122 may additionally be used to bioconvert added sulfoxy moieties and elemental sulfur to hydrogen sulfide. Line 128 provides sulfur or sulfur compounds to be reduced to hydrogen sulfide to anaerobic digester 122. As stated before, sulfuric and sulfurous acids are preferred and aid in maintaining a desired pH. The amount of sulfur moiety provided is preferably such that the biogas from anaerobic digester contains the sought amount of hydrogen sulfide to meet the requirements of the microorganisms in reactor 104. The amount to be provided can be calculated or may be in response to measurements. For instance, the hydrogen sulfide content of the off-gases can be determined and the amount of sulfur moiety provided increased or decreased to maintain the concentration in the off gases within a predetermined range. Often the amount of hydrogen sulfide required to be supplied to a reactor to meet nutrient needs of the microorganisms is in the range of 0.5 to 1.0% of the total cell mass grown in the fermenter.

The bioconversion of the sulfoxy moiety to hydrogen sulfide requires an electron donor. In most instances sufficient the electron donor exists in the anaerobic digester, e.g., from the biomass from the syngas fermentation. If additional electron donor is required, a suitable source of electron donor is the syngas. Conveniently a portion of the syngas may be passed to anaerobic digester 122 from line 102 via line 130. The amount of syngas required will depend in part upon the composition of the syngas and the amount of donor needed. As the syngas will be combined with the biogas for passage to reactor 104, the use of an excess amount of syngas can be used. Generally, about 1 to 10, say, about 2 to 5, volume percent of the syngas may be passed to anaerobic digester 122. The syngas provided by line 130 may also be used to sweep hydrogen sulfide from the anaerobic digestion liquor. In addition or alternatively, sweep gas may be provided by the recycling off-gas from line 112 passed to anaerobic digester 122 via line 131.

Cell disruption reactor 134 may be used to break open the cells, such as the Molecular Chemical Grinder technology offered by PMC Bio Tec, LLC, of Exton, Pa., and thereby enhance the rate of digestion of the solids. As shown, solids-containing liquid is withdrawn from anaerobic digester 122 via line 132, and subsequent to treatment is returned via line 136.

Where only anaerobic digester 122 is used, the solids-containing effluent from the digester can be directed to solids dewatering unit operation 154 which provides an aqueous effluent via line 156 for waste water treatment. A dewatered solids product is withdrawn via line 158 for solids disposal.

As depicted, the solids-containing effluent from anaerobic digester 122, which for purposes of the following description is an acidogenic digester, is passed via line 138 to electrodialysis reversal unit 140 for recovery of carboxylic acids. See, for instance, Electrodialysis (ED) and Electrodialysis Reversal (EDR), U.S. Department of the Interior, Bureau of Reclamation, Sep. 20, 2010. Other separation unit operations include, but are not limited to, electrodialysis, ion exchange membranes, ultrafiltration and liquid-liquid extraction. Fermentation broth is passed via line 142 from reactor 104 to ion exchange column 140 where carboxylic acid is recovered from the ion exchange resin and is returned via line 144 to reactor 104. Where ethanol is the sought oxygenated organic compound, the carboxylic acids are metabolized by microorganisms in the fermentation broth to generate additional ethanol and thus increase the overall conversion efficiency of syngas to ethanol.

The solids-containing effluent is then passed via line 146 from ion exchange column 140 to anaerobic digester 148 which is a methanogenic digester. Anaerobic digester 148 is maintained under methanogenic conditions. Any suitable microorganism for bioconversion of biomass to methane under anaerobic conditions may be used and frequently the anaerobic digestion liquor is self-inoculating. The conditions for the anaerobic digestion can vary depending upon the microorganisms used. Often, the temperature is between 25° and 60° C., frequently in the range of about 30° to 40° C. The pressure may be subatmospheric, atmospheric or super atmospheric, and is usually in the range of from about 90 to 1000 kPa absolute. Anaerobic digester 122 may be of any suitable design including, but not limited to, bubble column reactors; jet loop reactors; stirred tank reactors; trickle bed reactors; biofilm reactors; moving bed reactors; membrane reactors and static mixer reactors including, but not limited to, pipe reactors.

The methanogenic conditions in anaerobic digester 148 provide a methane-containing biogas and a slurry of digested solids. The methane-containing biogas will frequently contain about 50 to 70 volume percent methane and about 25 to 45 volume percent carbon dioxide with the balance being primarily water vapor. Often the hydrogen sulfide concentration is less than about 10 ppmv, preferably less than about 1 or 2 ppmv. The biogas is withdrawn from anaerobic digester 148 via line 150 and can be used for any suitable purpose, usually without further treatment to reduce sulfur content. As shown, the biogas is combined with the off-gas from reactor 104. The combined gases, which due to the combination with the methane-containing biogas, will have a slightly higher energy density. This gas may be thermally oxidized to provide heat, e.g., to dry biomass for gasification to generate syngas.

The slurry of digested solids is removed from anaerobic digester 148 via line 152 to be sent to dewatering unit operation 154. Water is removed from dewatering operation via line 156 and sent to waste water treatment. Dewatered solid are removed via line 158 for solids disposal.

Figure 2:
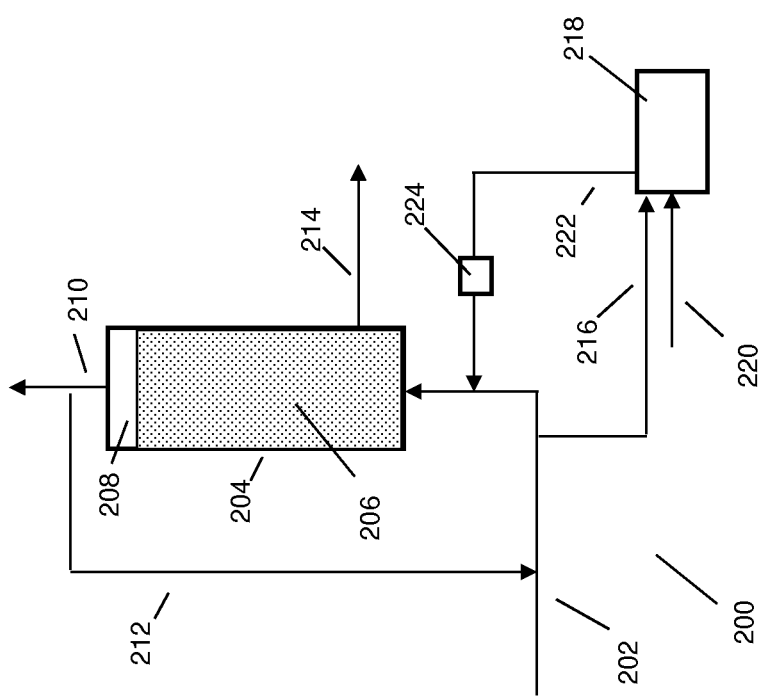
FIG. 2 is a schematic depiction of another apparatus capable of being used in accordance with this invention.

With respect to FIG. 2, apparatus 200 provides hydrogen sulfide as a nutrient to a fermentation broth for converting syngas to oxygenated organic compound. The syngas in line 202 is passed to reactor 204 containing fermentation broth 206. Fermentation broth is maintained under fermentation conditions and the syngas is provided therein in a manner to enhance mass transfer of hydrogen and carbon monoxide to the aqueous broth for bioconversion by microorganisms to oxygenated organic compound. Off-gas is withdrawn from head space 208 via line 210. A portion of the off-gas, if desired, can be recycled via line 212 to increase the conversion of syngas to product. Intermittently or continuously an aliquot portion of the fermentation broth 206 is withdrawn via line 214 for product recovery.

As shown, a portion of the syngas is provided via line 216 to sulfoxy reactor 218. Alternatively, a portion of the off-gas form the syngas fermenter may be used. Also provided to sulfoxy reactor 218 is sulfoxy moiety via line 220. For purposes of illustration only, the sulfoxy moiety is sulfuric acid. Sulfoxy reactor 218 contains microorganism for the bioconversion of sulfate to hydrogen sulfide. Biogas is withdrawn from sulfoxy reactor 218 via line 222 and is passed through filter 224 and then to reactor 204.

As described, the present invention provides a number of advantages, some of which have been described above and others which are inherent in the invention. Also, modifications may be proposed without departing from the teachings herein. Accordingly, the scope of the invention is only to be limited as necessitated by the accompanying claims.

It is claimed:

1. A process for fermenting syngas to oxygenated organic compound with integrated hydrogen sulfide supply comprising:
   a. passing syngas into a syngas fermentation reactor containing aqueous fermentation broth comprising microorganisms capable of bioconverting syngas to an oxygenated organic compound, to produce an oxygenated organic compound in the fermentation broth, biosolids comprising the microorganism, and an off-gas;
   b. removing a portion of the fermentation broth containing the oxygenated organic compound and biosolids from the syngas fermentation reactor;
   c. separating from said portion of the fermentation broth an aqueous biosolids-containing fraction with said fraction having a higher solids content than said portion of the fermentation broth;
   d. subjecting the aqueous biosolids-containing fraction to anaerobic digestion to biodegrade the solids to form an aqueous liquid phase containing degraded solids product and a gas product comprising hydrogen sulfide; and
   e. passing at least a portion of the gas product comprising hydrogen sulfide to the syngas fermentation reactor to provide at least a portion of sulfur nutrient for the microorganisms of step (a).

2. The process of claim 1 wherein the gas product further comprises carbon dioxide and methane and the off-gas comprises methane.

3. The process of claim 2 wherein the anaerobic digestion is methanogenic.

4. The process of claim 3 wherein a sulfur source comprising at least one of a compound comprising a sulfoxy moiety or elemental sulfur is supplied to step (d) and at least a portion of the sulfur source is bioconverted to hydrogen sulfide in step (d).

5. The process of claim 1 wherein at least a portion of said off-gas is supplied to step (d) to strip hydrogen sulfide from the aqueous liquid phase.

6. The process of claim 1 wherein the aqueous biosolids containing fraction is subjected to acidogenic anaerobic digestion to form an organic acid prior to forming the gas product.

7. The process of claim 6 wherein the pH of said aqueous biosolids containing fraction in step (d) is up to about 6.

8. The process of claim 7 wherein a sulfur source comprising at least one of a compound comprising a sulfoxy moiety or elemental sulfur is supplied to step (d) and at least a portion of the sulfur source is bioconverted to hydrogen sulfide in step (d).

9. The process of claim 8 wherein at least a portion of said off-gas is supplied to step (d) to strip hydrogen sulfide from the aqueous liquid phase.

10. The process of claim 6 wherein the organic acid produced is selectively removed and passed to the fermentation broth contained in the syngas fermentation reactor.

11. The process of claim 10 wherein the selective removal is effected by at least one of liquid-liquid exchange, ultrafiltration, membrane separation, ion exchange, electrodialysis, and electrodialysis reversal unit operation.

12. The process of claim 10 wherein after removal of the organic acid, the aqueous biosolids containing fraction is subjected to methanogenic anaerobic digestion conditions-to produce the gas product further comprising methane and a biodegraded aqueous solids product.

13. The process of claim 6 wherein after being subjected to acidogenic digestion the aqueous degraded solids product is subjected to methanogenic anaerobic digestion conditions to produce the gas product further comprising methane and a biodegraded aqueous solids product.

14. The process of claim 13 wherein at least a portion of the methane-containing gas product is combined with the off-gas.

15. The process of claim 13 wherein the methane-containing gas product contains less than 100 parts per million by volume of hydrogen sulfide.

16. The process of claim 1 wherein a sulfur source comprising at least one of a compound comprising a sulfoxy moiety or elemental sulfur is supplied to step (d) and at least a portion of the sulfur source is bioconverted to hydrogen sulfide in step (d).

17. The process of claim 16 wherein the portion of gas product passed to said syngas fermentation reactor maintains the hydrogen sulfide concentration of the off-gas in step (a) within a predetermined range.

* * * * *